(12) United States Patent
Hoyen et al.

(10) Patent No.: US 12,121,447 B2
(45) Date of Patent: Oct. 22, 2024

(54) ANATOMICAL RADIAL HEAD ELBOW PROSTHESIS

(71) Applicant: SIGNATURE ORTHOPAEDICS EUROPE LTD, Dublin (IE)

(72) Inventors: Harry Hoyen, Dublin (IE); William Duong, Dublin (IE); Chris Burgess, Dublin (IE); Declan Brazil, Lane Cove West (AU)

(73) Assignee: SIGNATURE ORTHOPAEDICS EUROPE LTD, Dublin (IE)

( * ) Notice: Subject to any disclaimer, the term of this patent is extended or adjusted under 35 U.S.C. 154(b) by 262 days.

(21) Appl. No.: 17/759,570

(22) PCT Filed: Jan. 31, 2021

(86) PCT No.: PCT/AU2021/050068
§ 371 (c)(1),
(2) Date: Jul. 27, 2022

(87) PCT Pub. No.: WO2021/151165
PCT Pub. Date: Aug. 5, 2021

(65) Prior Publication Data
US 2023/0270556 A1   Aug. 31, 2023

(30) Foreign Application Priority Data
Jan. 30, 2020  (AU) .................. 2020900240

(51) Int. Cl.
*A61F 2/38*  (2006.01)
*A61F 2/30*  (2006.01)

(52) U.S. Cl.
CPC .. *A61F 2/3804* (2013.01); *A61F 2002/30935* (2013.01); *A61F 2002/3809* (2013.01);
(Continued)

(58) Field of Classification Search
CPC .......... A61F 2/3804; A61F 2002/30935; A61F 2002/3809; A61F 2002/3818; A61F 2002/3827
See application file for complete search history.

(56) References Cited

U.S. PATENT DOCUMENTS

| 2014/0012388 A1 | 1/2014 | Brownhill et al. |
| 2014/0074246 A1 | 3/2014 | Huebner et al. |

(Continued)

FOREIGN PATENT DOCUMENTS

| WO | 2000013617 A1 | 3/2000 |
| WO | 2004066883 A2 | 8/2004 |

(Continued)

OTHER PUBLICATIONS

Acumed Anatomic Radial Head Solutions 2 [retrieved from internet on Sep. 3, 2020]. published on Oct. 2018.
(Continued)

*Primary Examiner* — Bruce E Snow
(74) *Attorney, Agent, or Firm* — INNOVATION CAPITAL LAW GROUP, LLP; Vic Lin

(57) ABSTRACT

There is disclosed herein radial head elbow prosthesis which is anatomically designed to improve anatomical conformity and function and reduce likelihood of dislocation. Depression centroid eccentricity and orientation and raised lateral bearing surface aspects of the present radial head improve tracking of the radial head prosthesis of the capitellum and reduce likelihood of dislocation thereof.

21 Claims, 5 Drawing Sheets

(52) U.S. Cl.
CPC ............... *A61F 2002/3818* (2013.01); *A61F 2002/3827* (2013.01)

(56) References Cited

U.S. PATENT DOCUMENTS

| | | |
|---|---|---|
| 2017/0095338 A1 | 4/2017 | Bergquist et al. |
| 2020/0253740 A1* | 8/2020 | Puncreobutr .......... A61B 17/15 |

FOREIGN PATENT DOCUMENTS

| | | |
|---|---|---|
| WO | 2005086939 A2 | 9/2005 |
| WO | 2006048520 A1 | 5/2006 |

OTHER PUBLICATIONS

Acumed Slide-Loc Anatomical Radial Head System [retrieved from internet on Aug. 19, 2020]. published on Oct. 27, 2016 (publication date retrieved from Meta Data of the pdf).
International Search Report & Written Opinion dated Apr. 6, 2021 from PCT Application No. PCT/AU2021/050068, 10 pages.
International-type search report dated Sep. 7, 2020 from Australia Application No. 2020900240, 13 pages.
Lalone, AL et al., 'Design of Anatomical Population-Based and Patient-Specific Radial Head Implants', The Journal of Hand Surgery, vol. 42 (11), No. 4 ,pp. 924.EI-924.EI 1, Published Nov. 2017.
Shannon, LS et al., 'Effect of Radial Head Implant Shape on Joint Contact Area and Location During Static Loading', The Journal of Hand Surgery, vol. 40, No. 4 ,pp. 716-722, Published 2015.

\* cited by examiner

ANATOMICAL RADIAL HEAD ELBOW PROSTHESIS

FIELD OF THE INVENTION

This invention relates generally to elbow prosthesis. More particularly, this invention relates to anatomical radial head elbow prosthesis.

BACKGROUND OF THE INVENTION

The elbow joint is a compound joint of the humerus, radius and ulna. A proximal head of the radius ("radial head") articulates proximally with the capitellum of the humerus (humero-radial joint) and medially with the radial notch of the ulna (radio-ulnar joint).

The radial head allows the radius to achieve distinct motions when the arm is flexed and extended when the hand is pronated or supinated. During flexion and extension the radial head articulates across the curved surface of the capitellum whilst the humero-ulnar joint functions as a hinge. When the hand is rotated between pronation and supination positions, the radial head pivots on the capitellum, and the side of the radial head turns in the radial notch.

A radial head elbow prosthesis is used to replace a damaged radial head and typically has a stem which is inserted into the radius and a head that articulates with the ulna and humerus.

Whereas radial heads have traditionally been generally circular in cross-section in the horizontal plane, radial heads nowadays include anatomically designed radial heads which help to improve function and motion.

The present invention seeks to provide elbow prosthesis which improves anatomical conformity and reduce likelihood of dislocation, which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE DISCLOSURE

There is provided herein radial head elbow prosthesis designed anatomically from cadaver investigation and digital CT scan reconstructions (digital segmentation) computer aided modelling studies to improve anatomical conformity and function and reduce likelihood of dislocation.

Depression centroid eccentricity and orientation and raised lateral bearing surface aspects of the present radial head were experimentally discovered to improve tracking of the radial head prosthesis of the capitellum and reduce likelihood of dislocation thereof.

Further aspects of the present prosthesis may ergonomically accommodate the annular ligament of the elbow, account for the anatomical geometry of the radial notch to improve surface contact therewith and conform to the anatomical geometry of the radial head of the radius bone.

Furthermore, the present radial head may be provided in differing sizes according to patient requirements but have certain geometric correlations therebetween which were discovered to increase anatomical conformity amongst patients.

The present prosthesis may further comprise a stem which may have lateral anatomical curvature, which may be polished for press fit (cementless) insertion, which self-locates securely within the proximal radial canal. The stem may be centrally located with respect to the radial head which was found to be better position for articulation and even distribution of rotational stress. Furthermore, the stem curvature may be directed away from the radial styloid towards the lateral side of Lister's tubercle, preferably approximately 30° radially offset with respect to the radial styloid.

With the foregoing in mind, according to one aspect, there is provided elbow prosthesis comprising a radial head having a superior dished capitellum bearing surface a medial-side radial notch bearing ulnar facet, the bearing surface defining a bearing surface centroid and having a depression formed therein forming a depression centroid, wherein the depression centroid is located anteriorly with respect to the surface centroid.

The ratio between the bearing surface centroid and the depression centroid and the depression centroid and a point at a rim of the bearing surface being closest the depression centroid may be more than 25%.

The ratio may be approximately 33%.

The bearing surface may be raised at a lateral side thereof.

The bearing surface may be non-circular in cross-section.

The bearing surface may have a lateral outermost point.

The lateral outermost point may coincide with a widest axis of the bearing surface.

The widest axis may be a mediolateral axis.

A min/max diameter ratio of the bearing surface may be greater than 95%.

The bearing surface may be ovular in cross section.

The depression may define a bearing axis perpendicularly at the bearing surface centroid and wherein the prosthesis may define a rotational axis and wherein the bearing axis may be angled with respect to the rotational axis.

The rotational axis and the bearing axis coincide superiorly with respect to the radial head.

The bearing axis may be angled with respect to the rotational axis by between 5-15°.

The rotational axis may be perpendicular to a horizontal plane.

The horizontal plane may be defined by a planar undersurface of the radial head.

A bearing plane defined by a rim of the bearing surface may be at an angle with respect to a horizontal plane being perpendicular to the rotational axis.

The rim may be coplanar with the bearing plane.

An undersurface of the radial head may be circular in cross-section.

An undersurface of the radial head may define an undersurface centroid which may be located anteriorly with respect to the bearing surface centroid.

An undersurface of the radial head may be planar.

The radial head may define an anterior face cross-sectional elevation profile which curves substantially uniformly from an undersurface of the radial head to the bearing surface.

The radial head may define a posterior face cross-sectional elevation profile which may define an s-bend overhang above which the posterior side transitions with less curvature and greater outward extent as compared to the anterior face.

The ulnar facet may define a cross-sectional elevation profile having an overhang.

The overhang may be located below a third of the height between the undersurface and the bearing surface.

The ulnar facet curves substantially uniformly above the overhang.

The ulnar facet curves uniformly outwardly towards the bearing surface above the overhang.

The radial head may define a lateral face cross-sectional profile having a lower section, an overhang and an upper section.

The ulnar facet may define a cross-sectional elevation profile having an overhang and wherein the overhang of the lateral face cross-sectional profile may be above the overhang of the medial ulnar facet.

The lower section may be substantially orthogonal with respect to a horizontal plane may define by an undersurface of the radial head.

The overhang locates substantially midway between the lower section and the upper section.

The radial extent of the lower section may be substantially co-radial with the resected radius bone once installed in use.

The depression may be anteroposteriorly asymmetrical in horizontal cross section.

The prosthesis may further comprise a differently sized radial head and wherein the min/max diameter ratio of the bearing surfaces thereof may be substantially constant.

The prosthesis may further comprise a differently sized radial head and wherein the ratio of diameters of the bearing surfaces and the offsets between the depression centroids and the bearing surface centroids thereof may be substantially constant.

The prosthesis may further comprise a differently sized radial head and wherein the ratio of diameters of bearing surfaces and heights of the radial heads may be substantially constant.

The prosthesis may further comprise a differently sized radial head and wherein the ratio of diameters of bearing surfaces and undersurfaces thereof may be substantially constant.

The prosthesis may further comprise a differently sized radial head and wherein the ratio of diameters of bearing surfaces and depressions thereof may be substantially constant.

The elbow prosthesis may further comprise a stem having posterolateral curvature.

The lateral curvature may comprise a superior and inferior portions and an elbow forming a transition therebetween.

The superior portion may be non-circular in cross-section.

The stem may define an axis offset with respect to the bearing surface centroid.

The radial head and the stem may be configured such that, when the stem is inserted in use, the stem may be orientated away from the radial styloid toward a lateral side of Lister's tubercle of the elbow.

The stem may be orientated more than 20° away from the radial styloid.

The stem may be orientated approximately 30° away from the radial styloid.

Other aspects of the invention are also disclosed.

BRIEF DESCRIPTION OF THE DRAWINGS

Notwithstanding any other forms which may fall within the scope of the present invention, preferred embodiments of the disclosure will now be described, by way of example only, with reference to the accompanying drawings in which.

DESCRIPTION OF EMBODIMENTS

Figure 1:
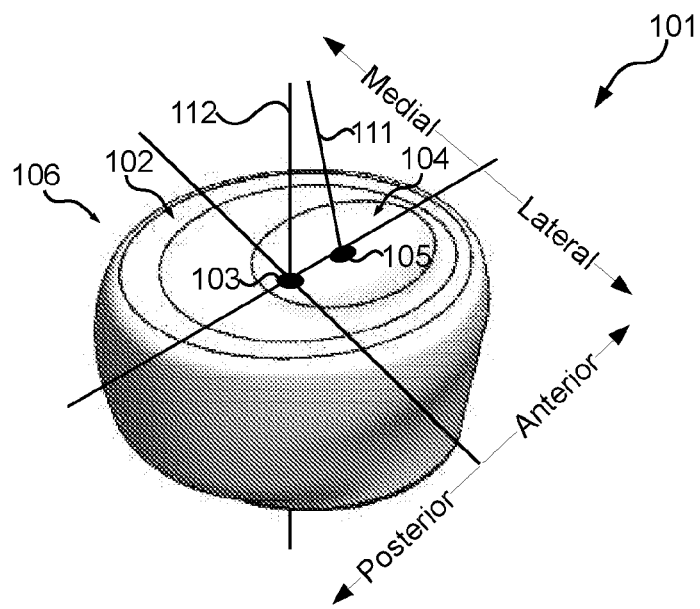
FIG. 1 shows a perspective view of an improved radial head in accordance with an embodiment.

A radial head 101 of elbow prosthesis 100 replaces a resected radial head of the radius bone and comprises a medial-side ulnar facet 106 which interfaces the radial notch of the ulnar bone.

Medial and derivatives thereof indicated in the figures indicate towards the ulnar bone and lateral and derivatives thereof indicate away from the ulnar bone. Furthermore, posterior, anterior and derivatives thereof indicate the respective orthogonal axes in horizontal plane.

The radial head 101 has a superior dished bearing surface 102 which articulates against the capitellum of the humerus bone.

The bearing surface 102 has a depression 104 formed therein. The bearing surface 102 defines a bearing surface centroid 103 which, with reference to FIG. 4, may be generally defined as being the centroid of the uppermost rim 107 of the bearing surface 102. Furthermore, the depression 104 forms a depression centroid 105 which, with reference to FIG. 4, may be defined as the centroid of a depression contour 108.

Figure 4:
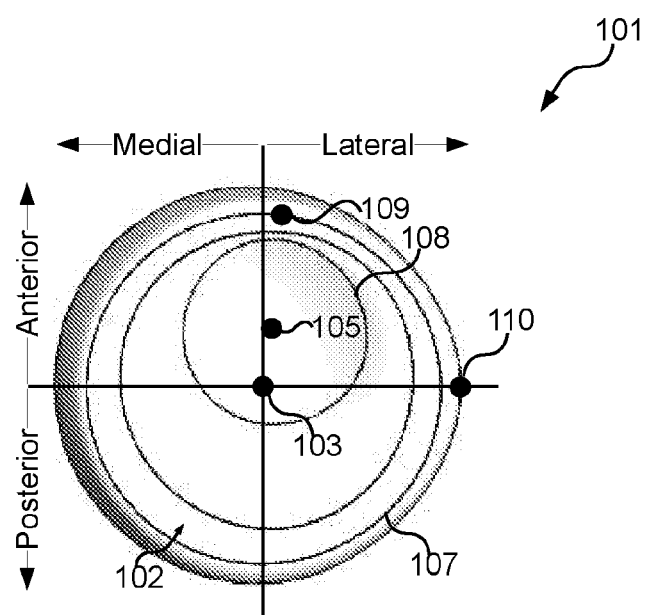
FIG. 4 shows a superior plan view of the radial head.

As shown in FIG. 4, the depression centroid 105 is located anteriorly with respect to the surface centroid 103.

The bearing surface centroid 105 may be eccentrically located more than a quarter of the way across the bearing surface 102 from the bearing surface centroid 103. In other words, the ratio of the length between the bearing surface centroid 103 and the depression centroid 105 and the depression centroid 105 and a closest point 109 of the rim may be more than 25%.

In a preferred embodiment, the depression centroid 105 is located approximately a third of the way across the bearing surface 102 from the bearing surface centroid 103. In other words, the ratio of the length between the bearing surface centroid 103 and the depression centroid 105 and the depression centroid and the closest point 109 of the rim may be approximately 33%.

Figure 2:
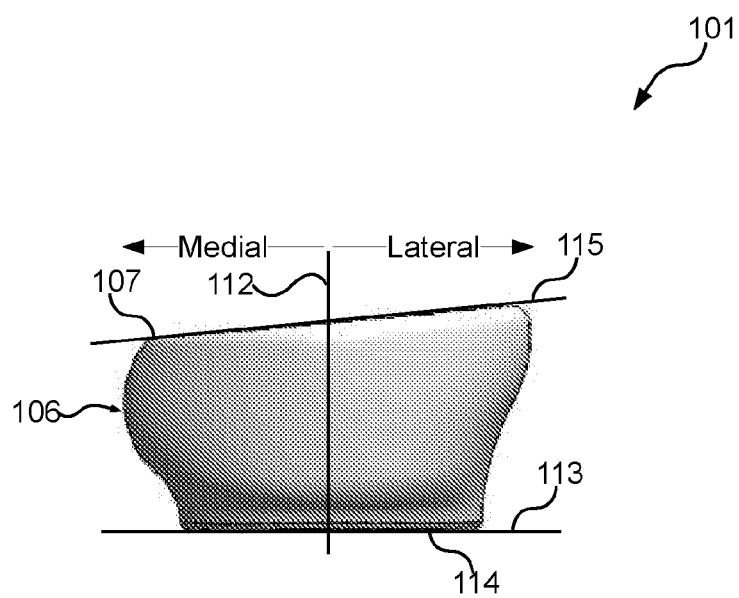
FIG. 2 shows a mediolateral elevation view of the radial head.

As best shown in FIG. 2, the bearing surface 102 may be raised at a lateral side thereof.

Referencing FIG. 4, the bearing surface 102 may be noncircular in cross-section and may have a lateral outermost point 110. As alluded to above, the bearing surface 102 may be defined as being within the uppermost rim 107 thereof. The min/max diameter ratio of the bearing surface 102 may be greater than 95%. Furthermore, the bearing surface 102 may be ovular in cross-section (i.e. symmetric about one axis only or egg shaped).

As best shown in FIG. 4, the bearing surface 102 may be wider mediolaterally as compared to anteroposteriorly and the outermost point 110 may coincide with the widest/mediolateral axis of the bearing surface 102.

As shown in FIG. 1, the depression 102 defines a bearing axis 111 perpendicularly at the bearing surface centroid 103. Furthermore, the radial head 101 may define a rotational axis 112. The rotational axis 112 may be the axis about which the radial head rotates when articulating with the capitellum. As is shown in FIG. 2, the rotational axis 112 may be perpendicular with respect to a horizontal plane 113 defined by a planar undersurface 114 of the head 101. The planar undersurface 114 may bear against a prepared planar surface of the resected radius.

As is illustrated in FIG. 1, the bearing axis 111 may be offset at an angle with respect to the rotational axis 112 with the bearing axis 111 and the rotational axis 112 coinciding superiorly with respect to the radial head 104. The bearing axis 111 may be angled with respect to the rotational axis 112 by between 5-15°.

As shown in FIG. 2, the bearing surface rim 107 may define a bearing surface plane 115 which is angled with respect to the horizontal plane 113. The bearing surface axis 111 may be perpendicular with respect to the bearing surface plane 115.

As is illustrated in FIG. 2, the rim 107 may be substantially coplanar with the bearing surface plane 115.

Figure 3:
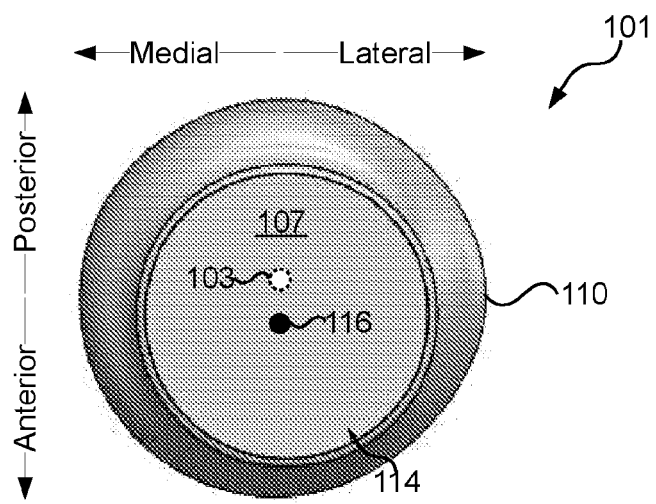
FIG. 3 shows an inferior plan view of the radial head.

With reference to FIG. 3, the undersurface 114 may be generally circular in cross-section. Furthermore, the undersurface 114 may define an undersurface centroid 116. The undersurface centroid 116 may be located anteriorly with respect to the bearing surface centroid 103.

Figure 5:
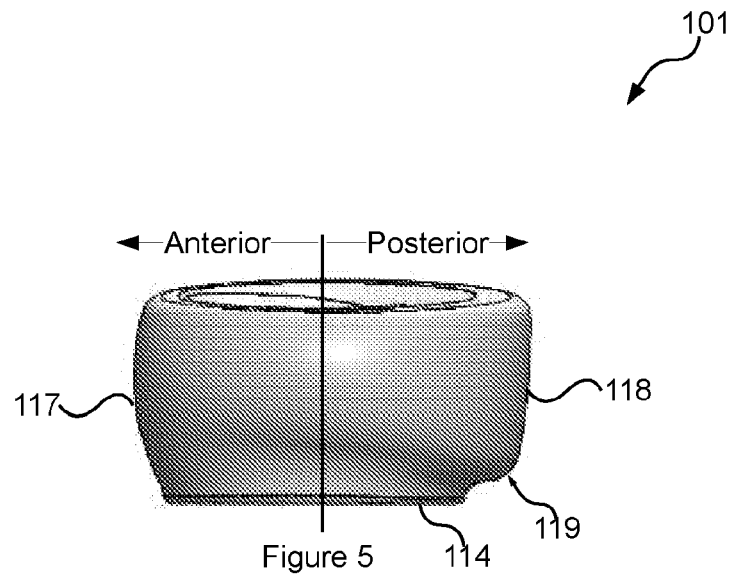
FIG. 5 shows an anteroposterior elevation view of the radial head.
Figure 6:
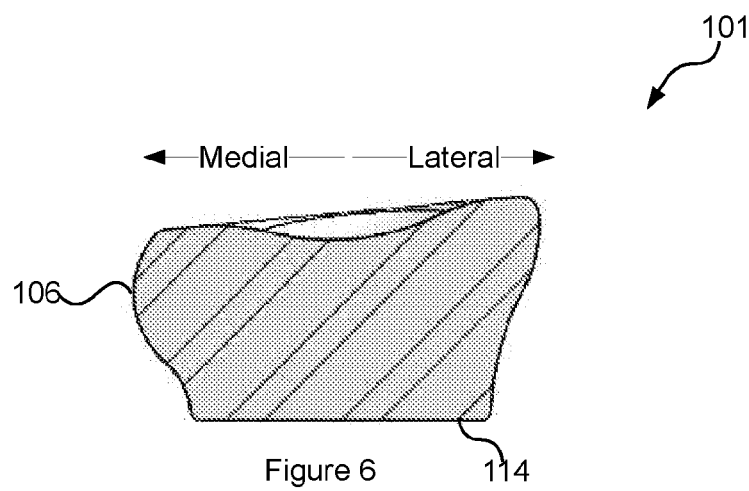
FIG. 6 shows a mediolateral cross-sectional view of the radial head.

As is shown in FIG. 5, the radial head 101 may define an anterior face 117 which has a cross-sectional elevation profile which curves substantially uniformly from the undersurface 114 to the bearing surface 102. A posterior side 118 may define a cross-sectional elevation profile defining an s-bend overhang 119 above which the posterior side 118 transitions with less curvature and greater outward extent as compared to the anterior face 117.

Figure 7:
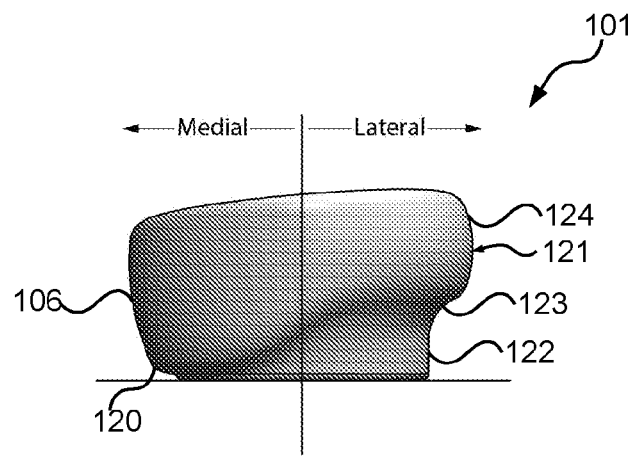
FIG. 7 shows a mediolateral cross-sectional view of the radial head in accordance with an embodiment.

FIG. 7 shows a cross-sectional elevation profile of the medial ulnar facet 106 according to an embodiment which defines an overhang 120 above which the ulnar facet 106 curves substantially uniformly and outwardly towards the bearing surface 102.

The lateral face 121 may define a cross-sectional elevation profile which defines a lower section 122, an overhang 123 and an upper section 124. The lower section 122 may be substantially orthogonal with respect to the horizontal plane 113 and the overhang 123 may locate substantially midway between the lower section 122 and the upper section 124. The radial extent of the lower section 122 may be designed to be substantially be co-radial with the resected radius bone thereunderneath to ergonomically interface the annular ligament.

With reference to FIG. 4, the depression contour 108 may be anteroposteriorly asymmetrical in horizontal cross section.

Differently sized radial heads 101 may be provided wherein the min/max diameter ratio of the bearing surface 102 remains substantially constant. In other words, with reference FIG. 4, the ratio of the mediolateral and anteroposterior width of the bearing surface 102 may remain substantially constant.

Furthermore, the ratio of diameter of the bearing surface 102 and offset between the depression centroid 105 and the bearing surface centroid 103 may remain substantially constant.

Furthermore, the ratio of diameters of the bearing surface 102 and undersurface 104 may remain substantially constant.

Furthermore, the ratio of diameters of the bearing surface 102 and the depression 104 may remain substantially constant.

Figure 8:
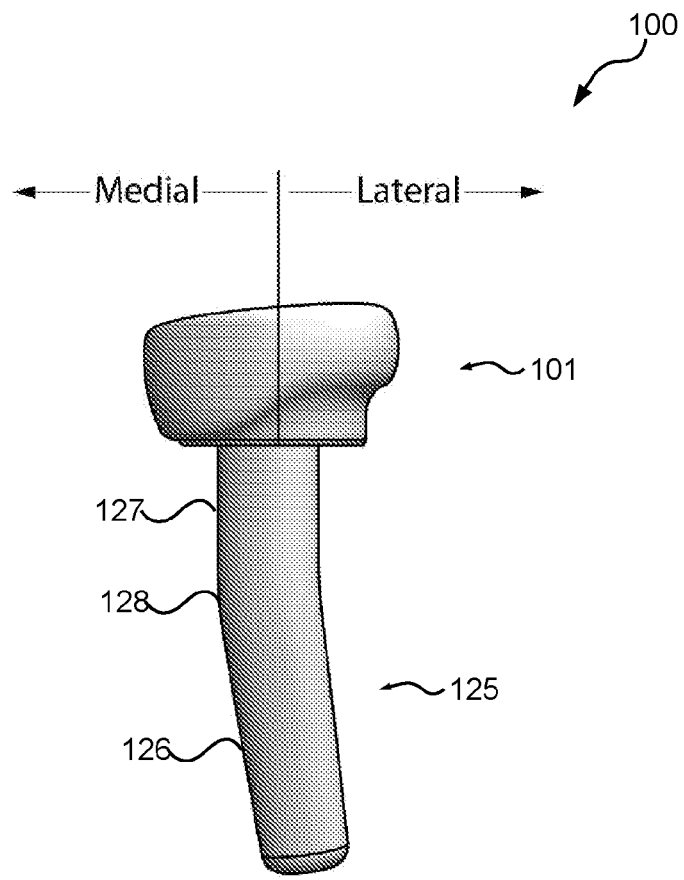
FIG. 8 shows a mediolateral side view of elbow prosthesis comprising a stem in accordance with an embodiment.

FIG. 8 shows a stem 125 integrally formed with the radial head 101 or attachable thereto. The stem 125 may have a smaller diameter than that of the undersurface 114 so as to expose an undersurface periphery thereabout for bearing against a prepared surface of the resected radius. The stem 125 may be polished and used for press fit (cementless) radial canal insertion.

Figure 9:
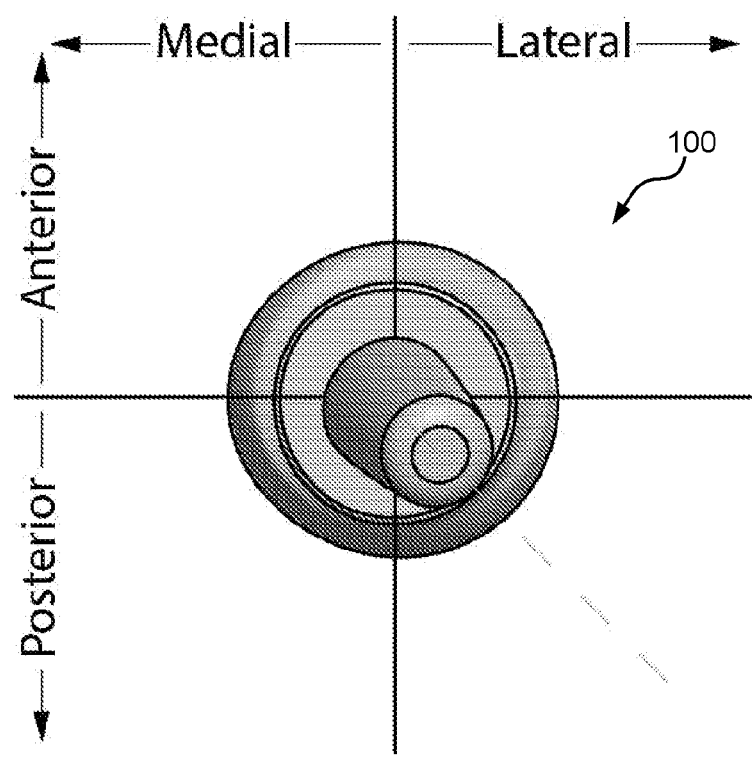
FIG. 9 shows an underside plan view of the elbow prosthesis of FIG. 6.

As shown in FIGS. 8 and 9, the stem 125 may have posterolateral anatomical curvature. The stem 125 may comprise a proximal section 127, a distal section 126 and an elbow 128 transition therebetween. The proximal section 127 may have sufficient length to transition the proximal radial canal isthmus.

As shown in FIG. 9, whereas a distal end 126 of the stem 125 may be circular in cross-section, a proximal end 127 thereof may be non-circular in cross-section, such as ovular.

Furthermore, a stem axis 127 may be offset with respect to the bearing surface centroid 103.

The foregoing description, for purposes of explanation, used specific nomenclature to provide a thorough understanding of the invention. However, it will be apparent to one skilled in the art that specific details are not required in order to practise the invention. Thus, the foregoing descriptions of specific embodiments of the invention are presented for purposes of illustration and description. They are not intended to be exhaustive or to limit the invention to the precise forms disclosed as obviously many modifications and variations are possible in view of the above teachings. The embodiments were chosen and described in order to best explain the principles of the invention and its practical applications, thereby enabling others skilled in the art to best utilize the invention and various embodiments with various modifications as are suited to the particular use contemplated. It is intended that the following claims and their equivalents define the scope of the invention.

The term "approximately" or similar as used herein should be construed as being within 10% of the value stated unless otherwise indicated.

The invention claimed is:

1. An elbow prosthesis comprising a radial head having a superior dished capitellum bearing surface and a medial-side radial notch bearing ulnar facet, the bearing surface defining a bearing surface centroid and having a depression formed therein forming a depression centroid, wherein the depression centroid is located anteriorly with respect to the surface centroid, wherein a ratio between the bearing surface centroid and the depression centroid and the depression centroid and a point at a rim of the bearing surface being closest the depression centroid is more than 25%.

2. The elbow prosthesis as claimed in claim 1, wherein the bearing surface is raised at a lateral side thereof and is non-circular in cross-section.

3. The elbow prosthesis as claimed in claim 1, wherein the bearing surface has a lateral outermost point which is along a mediolateral axis of the prosthesis.

4. The elbow prosthesis as claimed in claim 1, wherein a min/max diameter ratio of the bearing surface is greater than 95%.

5. The elbow prosthesis as claimed in claim 1, wherein the bearing surface is ovular in cross section and wherein an undersurface of the radial head is circular in cross-section.

6. The elbow prosthesis as claimed in claim 1, wherein the depression defines a bearing axis perpendicularly at the bearing surface centroid and wherein the prosthesis defines a rotational axis and wherein the bearing axis is angled with respect to the rotational axis.

7. The elbow prosthesis as claimed in claim 1, wherein the radial head defines an anterior face cross-sectional elevation profile which curves substantially uniformly from an undersurface of the radial head to the bearing surface and wherein the radial head defines a posterior face cross-sectional elevation profile which defines an s-bend overhang above which the posterior side transitions with less curvature and greater outward extent as compared to the anterior face.

8. The elbow prosthesis as claimed in claim 1, wherein the ulnar facet defines a cross-sectional elevation profile having an overhang and wherein the overhang is located below a third of the height between the undersurface and the bearing surface.

9. The elbow prosthesis as claimed in claim 1, wherein the radial head defines a lateral face cross-sectional profile having a lower section, an overhang and an upper section, wherein the ulnar facet defines a cross-sectional elevation profile having an overhang; wherein the overhang of the lateral face cross-sectional profile is above the overhang of the medial ulnar facet, wherein the lower section is substantially orthogonal with respect to a horizontal plane defines by an undersurface of the radial head, wherein the overhang locates substantially midway between the lower section and the upper section and wherein the radial extent of the lower section is substantially co-radial with the resected radius bone once installed in use.

10. The elbow prosthesis as claimed in claim 1, wherein the depression is anteroposteriorly asymmetrical in horizontal cross section.

11. The elbow prosthesis as claimed in claim 1, further comprising a differently sized radial head and wherein a min/max diameter ratio of the bearing surfaces thereof is substantially constant as compared to a min/max diameter ratio of the bearing surfaces of the radial head, wherein the differently sized radial head has a size different from a size of the radial head.

12. The elbow prosthesis as claimed in claim 1, further comprising a differently sized radial head and wherein a ratio of diameters of the bearing surfaces and offsets between depression centroids and bearing surface centroids thereof is substantially constant as compared to a ratio of diameters of the bearing surfaces and offsets between depression centroids and bearing surface centroids of the radial head, wherein the differently sized radial head has a size different from a size of the radial head.

13. The elbow prosthesis as claimed in claim 1, further comprising a differently sized radial head and wherein a ratio of diameters of bearing surfaces and heights thereof is substantially constant as compared to a ratio of diameters of bearing surfaces and heights of the radial head, wherein the differently sized radial head has a size different from a size of the radial head.

14. The elbow prosthesis as claimed in claim 1, further comprising a differently sized radial head and wherein a ratio of diameters of bearing surfaces and undersurfaces thereof is substantially constant as compared to a ratio of diameters of bearing surfaces and undersurfaces of the radial head, wherein the differently sized radial head has a size different from a size of the radial head.

15. The elbow prosthesis as claimed in claim 1, further comprising a differently sized radial head and wherein a ratio of diameters of bearing surfaces and depressions thereof is substantially constant as compared to a ratio of diameters of bearing surfaces and depressions of the radial head, wherein the differently sized radial head has a size different from a size of the radial head.

16. The elbow prosthesis as claimed in claim 1, further comprising a stem having posterolateral curvature and wherein the posterolateral curvature comprises superior and inferior portions and an elbow forming a transition therebetween.

17. The elbow prosthesis as claimed in claim 16, wherein the superior portion is non-circular in cross-section and wherein the stem defines an axis offset with respect to the bearing surface centroid.

18. The elbow prosthesis as claimed in claim 16, wherein the radial head and the stem are configured such that, when the stem is inserted in use, the stem is orientated away from the radial styloid toward a lateral side of Lister's tubercle of the elbow.

19. The elbow prosthesis as claimed in claim 1, wherein an undersurface of the radial head defines an undersurface centroid which is located anteriorly with respect to the bearing surface centroid.

20. An elbow prosthesis comprising a radial head having a superior dished capitellum bearing surface and a medial-side radial notch bearing ulnar facet, the bearing surface defining a bearing surface centroid and having a depression formed therein forming a depression centroid, wherein the depression centroid is located anteriorly with respect to the surface centroid, wherein the radial head defines an anterior face cross-sectional elevation profile which curves substantially uniformly from an undersurface of the radial head to the bearing surface and wherein the radial head defines a posterior face cross-sectional elevation profile which defines an s-bend overhang above which the posterior side transitions with less curvature and greater outward extent as compared to the anterior face.

21. An elbow prosthesis comprising a radial head having a superior dished capitellum bearing surface and a medial-side radial notch bearing ulnar facet, the bearing surface defining a bearing surface centroid and having a depression formed therein forming a depression centroid, wherein the depression centroid is located anteriorly with respect to the surface centroid, wherein the elbow prosthesis further comprises a stem having posterolateral curvature and wherein the posterolateral curvature comprises superior and inferior portions and an elbow forming a transition therebetween.

* * * * *